(12) United States Patent
Gopalaswamy et al.

(10) Patent No.: US 11,304,616 B2
(45) Date of Patent: Apr. 19, 2022

(54) HEART RATE DETECTION SYSTEM AND WEARABLE DEVICE USING THE SAME

(71) Applicant: LITE-ON SINGAPORE PTE. LTD., Midview (SG)

(72) Inventors: Arakere Dinesh Gopalaswamy, Bangalore (IN); Mon-Oo Win, Singapore (SG); Jing-Yuan Huang, Melaka (MY)

(73) Assignee: LITE-ON SINGAPORE PTE. LTD., Midview (SG)

( * ) Notice: Subject to any disclaimer, the term of this patent is extended or adjusted under 35 U.S.C. 154(b) by 642 days.

(21) Appl. No.: 16/120,344

(22) Filed: Sep. 3, 2018

(65) Prior Publication Data
US 2020/0069201 A1   Mar. 5, 2020

(51) Int. Cl.
*A61B 5/024*   (2006.01)
*A61B 5/00*    (2006.01)

(52) U.S. Cl.
CPC ...... *A61B 5/02438* (2013.01); *A61B 5/02416* (2013.01); *A61B 5/681* (2013.01); *A61B 5/721* (2013.01); *A61B 5/7225* (2013.01); *A61B 5/7257* (2013.01); *A61B 2560/0223* (2013.01); *A61B 2560/0247* (2013.01)

(58) Field of Classification Search
CPC ............ A61B 5/02438; A61B 5/02416; A61B 5/7257; A61B 5/721; A61B 5/7225; A61B 5/681; A61B 2560/0247; A61B 2560/0223
See application file for complete search history.

(56) References Cited

U.S. PATENT DOCUMENTS

| 2003/0181817 | A1* | 9/2003 | Mori | A61B 5/0002 600/500 |
| 2015/0018636 | A1* | 1/2015 | Romesburg | A61B 5/024 600/301 |
| 2015/0305674 | A1* | 10/2015 | McPherson | A61B 5/4875 600/301 |
| 2018/0279958 | A1* | 10/2018 | Pamula | A61B 5/11 |
| 2020/0205680 | A1* | 7/2020 | Boukhayma | H04N 5/3745 |

OTHER PUBLICATIONS

Gdansk University of Technology and Air Force Academy in Deblin, "Multitask Noisy Speech Enhancement System", 2004, https://sound.eti.pg.gda.pl/denoise/noise.html (Year: 2004).*
Kamath et al., "A multi-band spectral subtraction method for enhancing speech corrupted by colored noise." ICASSP. vol. 4. 2002. (Year: 2002).*

* cited by examiner

*Primary Examiner* — Jacqueline Cheng
*Assistant Examiner* — Tho Q Tran
(74) *Attorney, Agent, or Firm* — Li & Cai Intellectual Property (USA) Office

(57) ABSTRACT

Disclosed are a heart rate detection system and a wearable device using the same. The heart rate detection system includes a light emitting unit, a light sensor and a processor. The light emitting unit emits a light to a human body. The light sensor senses a reflected light of the light and accordingly generates a first electric signal. The processor calculates the low-frequency noise signal and the high-frequency noise signal of the first electric signal, and removes them. After that, the processor executes a peak detection with respect to the first electric signal to calculate peak values of the first electric signal, and calculate a heart rate based on the time intervals among the peak values.

6 Claims, 6 Drawing Sheets

HEART RATE DETECTION SYSTEM AND WEARABLE DEVICE USING THE SAME

BACKGROUND OF THE INVENTION

1. Field of the Invention

The present disclosure relates to a heart rate detection system and a wearable device using the same; in particular, to a heart rate detection system and a wearable device that are less affected by noises caused by environmental factors.

2. Description of Related Art

With the development of technology, many kinds of wearable electronic devices have become available to the public. One such example is the popular sports bracelet. Generally, aside from functions offered by different applications, most sports bracelets function as pedometers, heart rate detectors, or sleep quality detectors.

Currently, the sports bracelets detect the heart rate of a user by using Photoplethysmography (PPG). However, heart rate detection with PPG are often inaccurate due to interferences caused by environmental factors, such as sweat, or the manner which the sports bracelet contacts the human skin. For a sports bracelet using PPG to detect the heart rate of a user, there must be a calibration mechanism or a compensation mechanism to remove noises caused by the environmental factors. The better the calibration mechanism or the compensation mechanism is designed, the more precisely the heart rate of the user can be detected by the sports bracelet.

SUMMARY OF THE INVENTION

The present disclosure provides a heart rate detection system. The heart rate detection system includes at least one light emitting unit, a light sensor and a processor, and the processor is coupled to the light sensor and the light emitting unit. The light emitting unit emits a light to a human body. The light sensor senses a reflected light of the light and accordingly generates a first electric signal. The processor is configured to: convert the first electric signal from a time-domain signal to a frequency-domain signal; calculate a low-frequency noise signal according to the first electric signal, and subtract the low-frequency noise signal from the first electric signal; calculate a high-frequency noise signal according to the first electric signal, and subtract the high-frequency noise signal from the first electric signal; convert the first electric signal from the frequency-domain signal to the time-domain signal; execute a peak detection with respect to the first electric signal according to a first sampling rate, and calculate a plurality of peak values of the first electric signal; and calculate a plurality of time intervals among the peak values according to the first sampling rate and the peak values, and calculate a heart rate based on the time intervals.

Also, the present disclosure provides another heart rate detection system. The heart rate detection system includes at least one light emitting unit, a light sensor, a motion sensor and a processor, and the processor is coupled to the light emitting unit, the light sensor and the motion sensor. The light emitting unit emits a light to a human body. The light sensor senses a reflected light of the light and accordingly generates a first electric signal. The motion sensor captures a motion data of the human body and generates a second electric signal according to the motion data. The processor is configured to: convert the first electric signal and the second electric signal from time-domain signals to frequency-domain signals; normalize the first electric signal and the second electric signal to make the amplitude of the first electric signal and the amplitude of the second electric signal equal; calculate and extend a frequency range of the first electric signal and a frequency range of the second electric signal by using an extrapolation method, and filter the first electric signal and the second electric signal; sample the first electric signal and the second electric signal to obtain a first discrete value list and a second discrete value list, wherein the first discrete value list and the second discrete value list respectively include a plurality of discrete values; calculate a dominant value according to the discrete values in the first discrete value list and the discrete values in the second discrete value list; and calculate a heart rate according to the dominant value.

Moreover, the present disclosure provides a wearable device. The wearable device includes any of the heart rate detection systems described above to instantly detect a heart rate of a user wearing the wearable device.

The heart rate detection system and the wearable device in the present disclosure have advantages as described below. In the present disclosure, the electric signal generated by the light sensor, despite being affected by noises caused by environmental factors, can be calibrated, so that the heart rate of a user can be precisely calculated according to the calibrated electric signal.

For further understanding of the present disclosure, reference is made to the following detailed description illustrating the embodiments of the present disclosure. The description is only for illustrating the present disclosure, not for limiting the scope of the claim.

BRIEF DESCRIPTION OF THE DRAWINGS

Embodiments are illustrated by way of example and not by way of limitation in the figures of the accompanying drawings, in which like references indicate similar elements and in which.

DETAILED DESCRIPTION OF EXEMPLARY EMBODIMENTS

The aforementioned illustrations and following detailed descriptions are exemplary for the purpose of further explaining the scope of the present disclosure. Other objectives and advantages related to the present disclosure will be illustrated in the subsequent descriptions and appended drawings. In these drawings, like references indicate similar elements.

It will be understood that, although the terms first, second, third, and the like, may be used herein to describe various elements, these elements should not be limited by these terms. These terms are only to distinguish one element from another element, and the first element discussed below could be termed a second element without departing from the teachings of the instant disclosure. As used herein, the term "and/or" includes any and all combinations of one or more of the associated listed items.

[One Embodiment of the Heart Rate Detection System]

Figure 1:
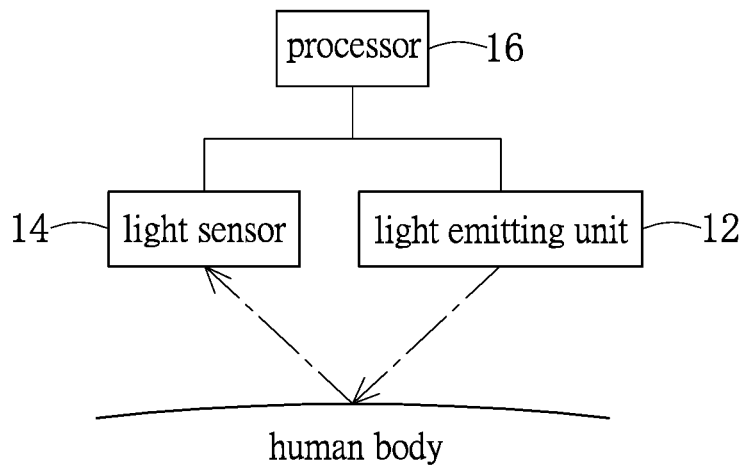
FIG. 1 shows a block diagram of a heart rate detection system according to one embodiment of the present disclosure.

FIG. 1 shows a block diagram of a heart rate detection system according to one embodiment of the present disclosure.

The heart rate detection system provided by this embodiment is usually configured in a wearable device, such as a smart watch, a sports bracelet, and the like. However, how a user wears the wearable device is not restricted herein. For example, the user can wear the wearable device on his wrist.

As shown in FIG. 1, the heart rate detection system includes at least one light emitting unit 12, a light sensor 14 and a processor 16, and the processor 16 is coupled to the light sensor 14 and the light emitting unit 12. The heart rate detection system instantly detects the heart rate of a user by using the PPG (Photoplethysmography; PPG). In brief, in this embodiment, the light emitting unit 12 emits a light to a human body. Then, the light sensor 14 detects a reflected light of the light, and accordingly generates a first electric signal. Finally, the processor 16 calculates the heart rate of the user according to the first electric signal. For example, the light emitting unit 12 can be a green light LED (Light Emitted Diode; LED). The wavelength of the green light is roughly within the range of 500 nm-550 nm, and thus the green light will not penetrate too deeply into the human body but can be almost fully absorbed by the hemoglobin.

It is worth mentioning that, in addition to the PPG; when calculating the heart rate of the user according to the first electric signal received from the light sensor, the processor 16 also uses another operation method to cancel noises caused by environmental factors, such that the heart rate of the user can be precisely detected.

In the following descriptions, the operation method to cancel noises caused by environmental factors is illustrated.

Figure 2:
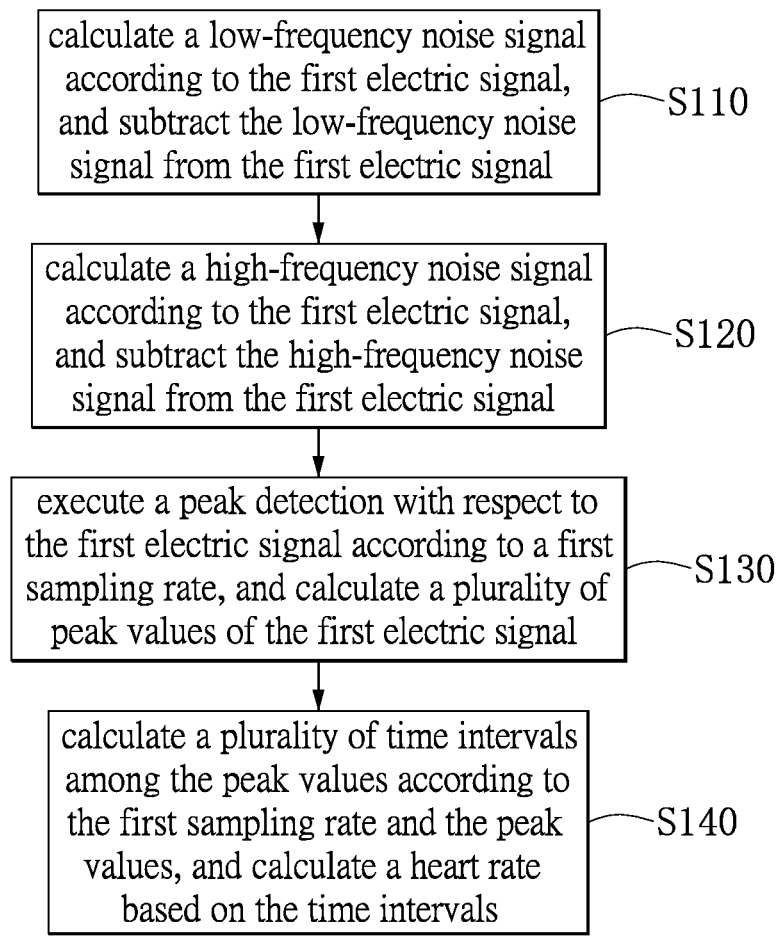
FIG. 2 and FIG. 3 are flow charts showing steps of the heart rate calculation executed by the processor of the heart rate detection system in FIG. 1.
Figure 3:
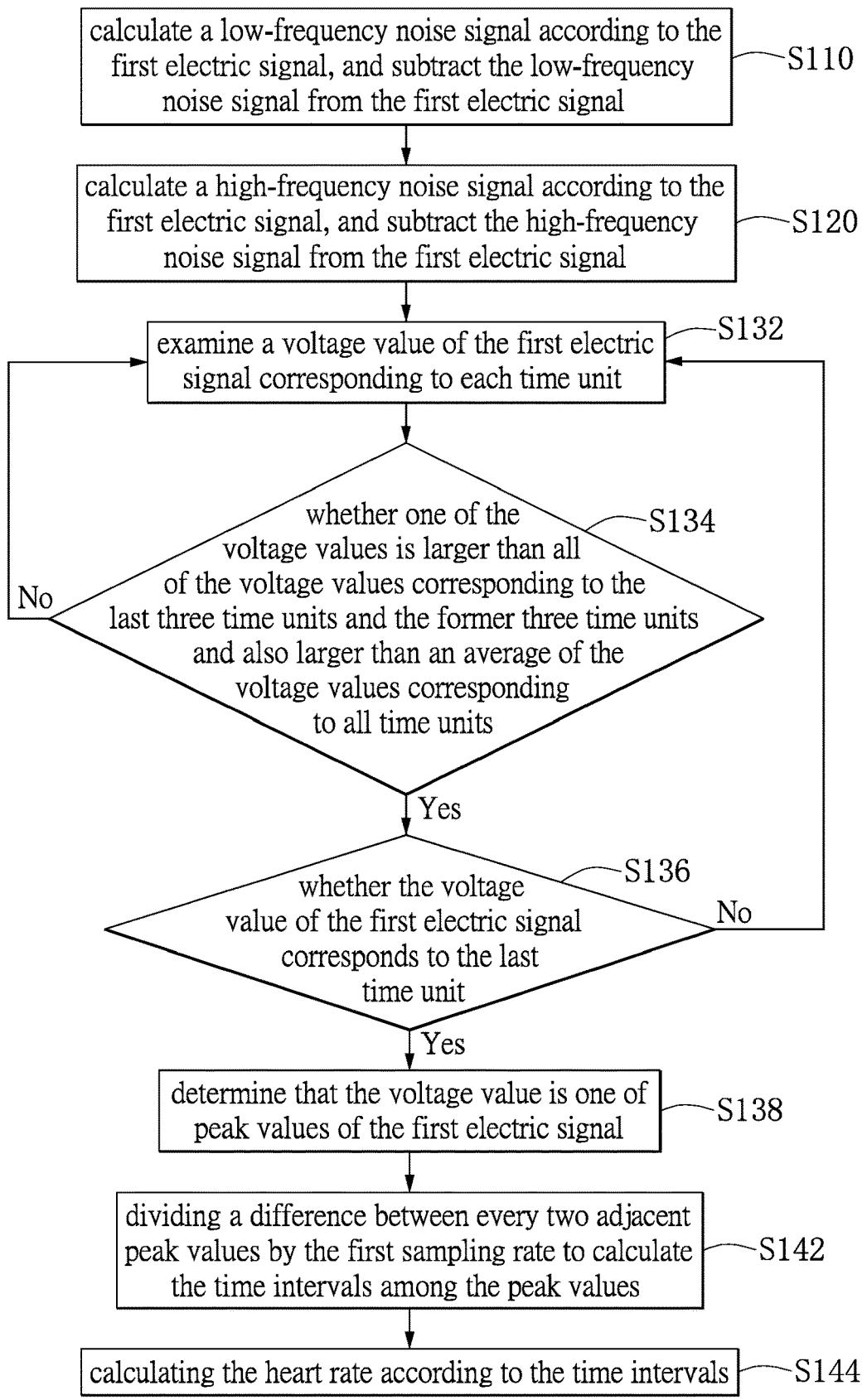

FIG. 2 and FIG. 3 are flow charts showing steps of the heart rate calculation executed by the processor of the heart rate detection system in FIG. 1.

In brief, the heart rate detection system provided by this embodiment calculates the heart rate of the user according to the first electric signal received from the light sensor by removing the noises from the first electric signal, and then calculating the heart rate of the user according to the first electric signal to eliminate any noise caused by the environment.

It should be noted that, the noises caused by the environmental factors may be low-frequency signals or high-frequency signals. For example, low-frequency noises may be caused by a slow arm swing or slow body waves, and the high-frequency noises may be caused by a quick arm swing or quick body waves. Thus, as shown in FIG. 2, after the processor 16 receives the first electric signal from the light sensor 14, the processor 16 first executes the step S110 and the step S120 to remove the low-frequency noises or the high-frequency noises caused by the environmental factors. In the operation for removing the noises, before the step S110 and the step S120, the processor 16 converts the first electric signal from a time-domain signal to a frequency-domain signal.

To remove the low-frequency noises caused by the environmental factors, the processor 16 calculates the low-frequency noise signal by using a low-frequency noise equation, and then subtracts the low-frequency noise signal from the first electric signal. In this embodiment, the low-frequency noise equation can be as follows:

$$Y[i] = \frac{\sum_{j=0}^{M-1} X[i+j]}{M}$$

In this low-frequency noise equation, Y[i] is the low-frequency noise signal, X[i+j] is the first electric signal, and M is a sampling number.

Similarly, to remove the high-frequency noises caused by the environmental factors, the processor 16 calculates the high-frequency noise signal by using a high-frequency noise equation, and then subtracts the high-frequency noise signal from the first electric signal. In this embodiment, the high-frequency noise equation can be as below:

$$S[i] = \frac{\sum_{j=0}^{M-1} Z[i+j]}{M}$$

In this high-frequency noise equation, S[i] is the high-frequency noise signal, Z[i+j] is the first electric signal having the low-frequency noise signal removed, and M is the sampling number.

After the processor 16 makes the low-frequency noise signal and the high-frequency noise signal removed from the first electric signal, the processor 16 executes the step S130 to detect peak values of the first electric signal. Detecting peak values of the first electric signal is to find the timing of every beat of the heart. In short, the processor 16 can obtain a plurality of peak values by detecting the peak values of the first electric signal, and the timing when one peak value occurs is the timing of one beat of the heart. Before the processor 16 detects peak values of the first electric signal, it converts the first electric signal back to a time-domain signal.

As shown in FIG. 3, the step S130 can be further divided into steps S132~S138. When detecting the peak values of the first electric signal, the processor 16 examines a voltage value of the first electric signal corresponding to each time unit, which is the step S132. It should be noted that, the time unit is a reciprocal of the first sampling rate. Specifically, the processor 16 divides the first electric signal based on this time unit so that each time unit corresponds to one voltage value of the first electric signal. Then, the processor 16 can examine the voltage value of the first electric signal corresponding to each time unit.

The processor 16 determines which voltage value is a peak value by executing the step S134. In the step S134, the processor 16 determines whether a voltage value corresponding to one time unit is larger than all of the voltage values corresponding to the last three time units and the next three time units, and whether said voltage value is also larger than an average of the voltage values corresponding to all time units. If said voltage value is larger than all of the voltage values corresponding to the last three time units and the next three time units, and is also larger than an average of the voltage values corresponding to all time units, the processor 16 determines that the voltage value is one of the peak values of the first electric signal.

However, if the processor 16 determines that the voltage value is not larger than all of the voltage values corresponding to the last three time units or is not larger than all of the voltage values corresponding to the next three time units, or the processor 16 determines that the voltage value is not larger than the average of the voltage values corresponding to all time units, the processor 16 determines that the voltage value is not one of the peak values of the first electric signal. Then, the processor 16 examines a voltage value corresponding to the next time unit.

After executing the step S314, the processor 16 further executes the step S316 to determine whether the voltage value of the first electric signal corresponds to the last time unit. If the voltage value of the first electric signal does not correspond to the last time unit, the processor 16 examines a voltage value corresponding to the next time unit. On the other hand, if voltage value of the first electric signal does correspond to the last time unit, the processor 16 ends the peak detection.

After the processor 16 ends the peak detection for the first electric signal and calculates a plurality of peak values, the processor 16 executes the step S140 to calculate the heart rate of the user according to the peak values. As shown in FIG. 3, the step S140 can be further divided to the steps S142~S144. Specifically speaking, the processor 16 executes the step S142 to calculate a plurality of time intervals among the peak values of the first electric signal. To calculate the time intervals among the peak values of the first electric signal, the processor 16 divides a difference between every two adjacent peak values by the first sampling rate. Then, the processor 16 executes the step S144 to convert the time intervals into the heart rate of the user. The processor 16 converts the time intervals into the heart rate of the user according to the time intervals and a first heart rate conversion equation, and the first heart rate conversion equation is as follows.

$$BPM = \frac{2*60}{T\left[\frac{n}{2}\right] + T\left[\frac{n}{2}+1\right]}$$

In the above equation, BPM is the heart rate, T is the difference between two adjacent peak values, and n is the number of the peak values.

According to the above descriptions, the heart rate detection system provided by this embodiment can calibrate the first electric signal generated by the light sensor by removing the low-frequency noise signals or the high-frequency noise signals caused by the environmental factors. Therefore, the heart rate detection system can precisely calculate the heart rate of the user according to the calibrated first electric signal.

[Another Embodiment of the Heart Rate Detection System]

Figure 4:
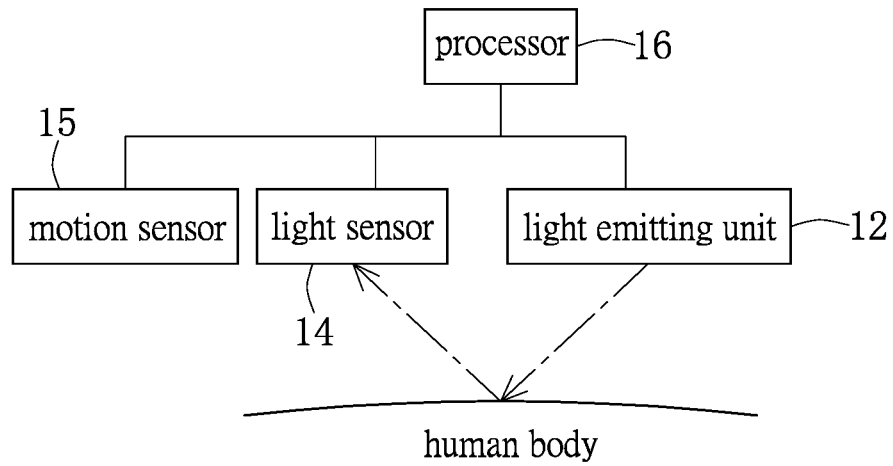
FIG. 4 shows a block diagram of a heart rate detection system according to another embodiment of the present disclosure.

FIG. 4 shows a block diagram of a heart rate detection system according to another embodiment of the present disclosure.

The heart rate detection system provided by this embodiment is usually configured in a wearable device, such as a smart watch, a sports bracelet and the like. However, how a user wears the wearable device is not restricted herein. For example, the user can wear the wearable device on his wrist.

To effectively find the noises and remove them, different from the heart rate detection system provided in the above embodiment, the heart rate detection system provided in this embodiment further includes a motion sensor. By using the motion sensor, the heart rate detection system can capture a motion data of the human body, take the motion data as a comparison data to find noises in the first electric signal, and remove the noises from the first electric signal. Compared with the heart rate detection system provided in the above embodiment that calculates a low-frequency noise signal or a high-frequency noise signal based on the first electric signal and removes it, the heart rate detection system provided in this embodiment can detect the user's heart rate more precisely.

As shown in FIG. 4, the heart rate detection system provided in this embodiment includes at least one light emitting unit 12, a light sensor 14, a motion sensor 15 and a processor 16, and the processor 16 is coupled to the light sensor 14, the motion sensor 15 and the light emitting unit 12.

The heart rate detection system instantly detects the heart rate of a user also by using the PPG (Photoplethysmography; PPG). In brief, in this embodiment, the light emitting unit 12 emits a light to a human body. Then, the light sensor 14 detects a reflected light of the light, and accordingly generates a first electric signal. At the same time, the motion sensor 15 captures a motion data of the human body and accordingly generates a second electric signal. The heart rate detection system provided by this embodiment calculates the heart rate of the user according to the first electric signal generated by the light sensor 14 and the second electric signal generated by the motion sensor 15.

Compared with the heart rate detection system provided by the previous embodiment, the heart rate detection system provided by this embodiment additionally has the motion sensor 15, and thus the processor 16 of the heart rate detection system provided by this embodiment uses a different operation method to calculate the heart rate of the user.

Figure 5:
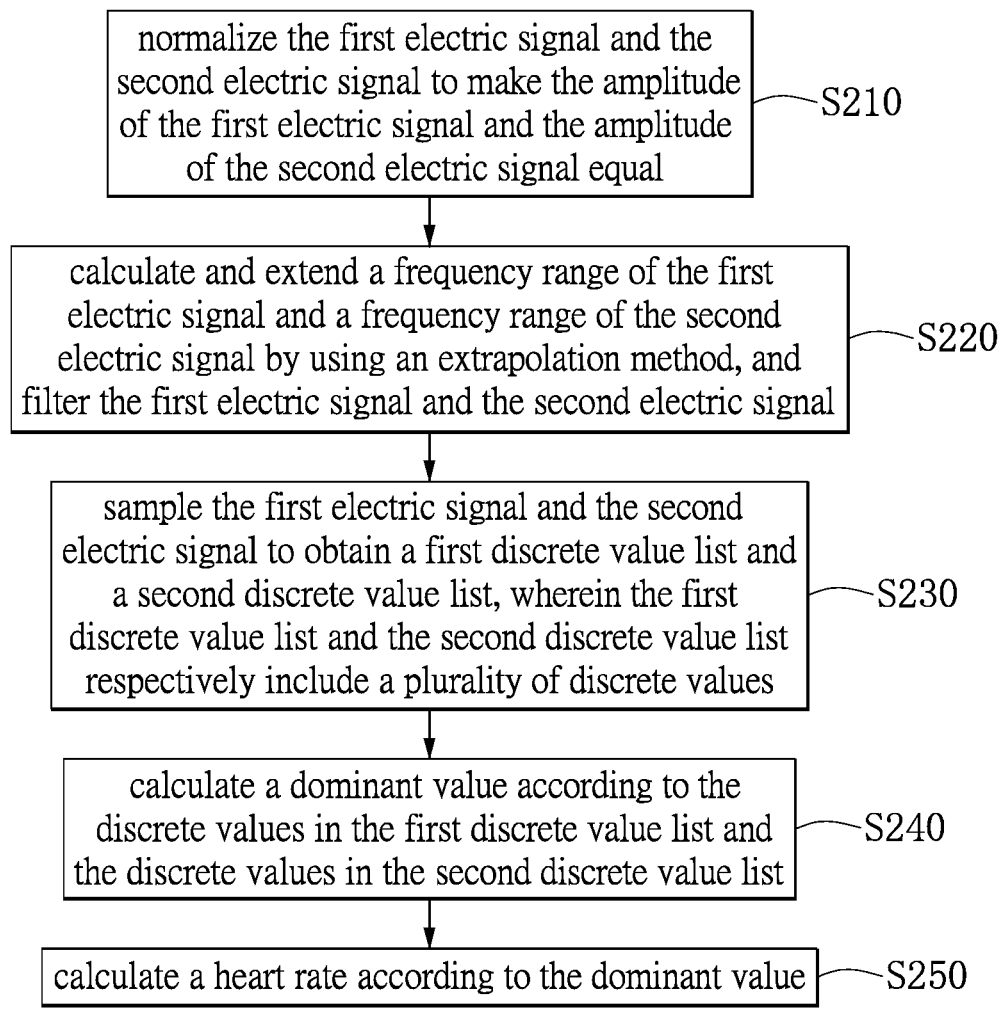
FIG. 5, FIG. 6A and FIG. 6B are flow charts showing steps of the heart rate calculation executed by the processor of the heart rate detection system in FIG. 4.
Figure 6A:
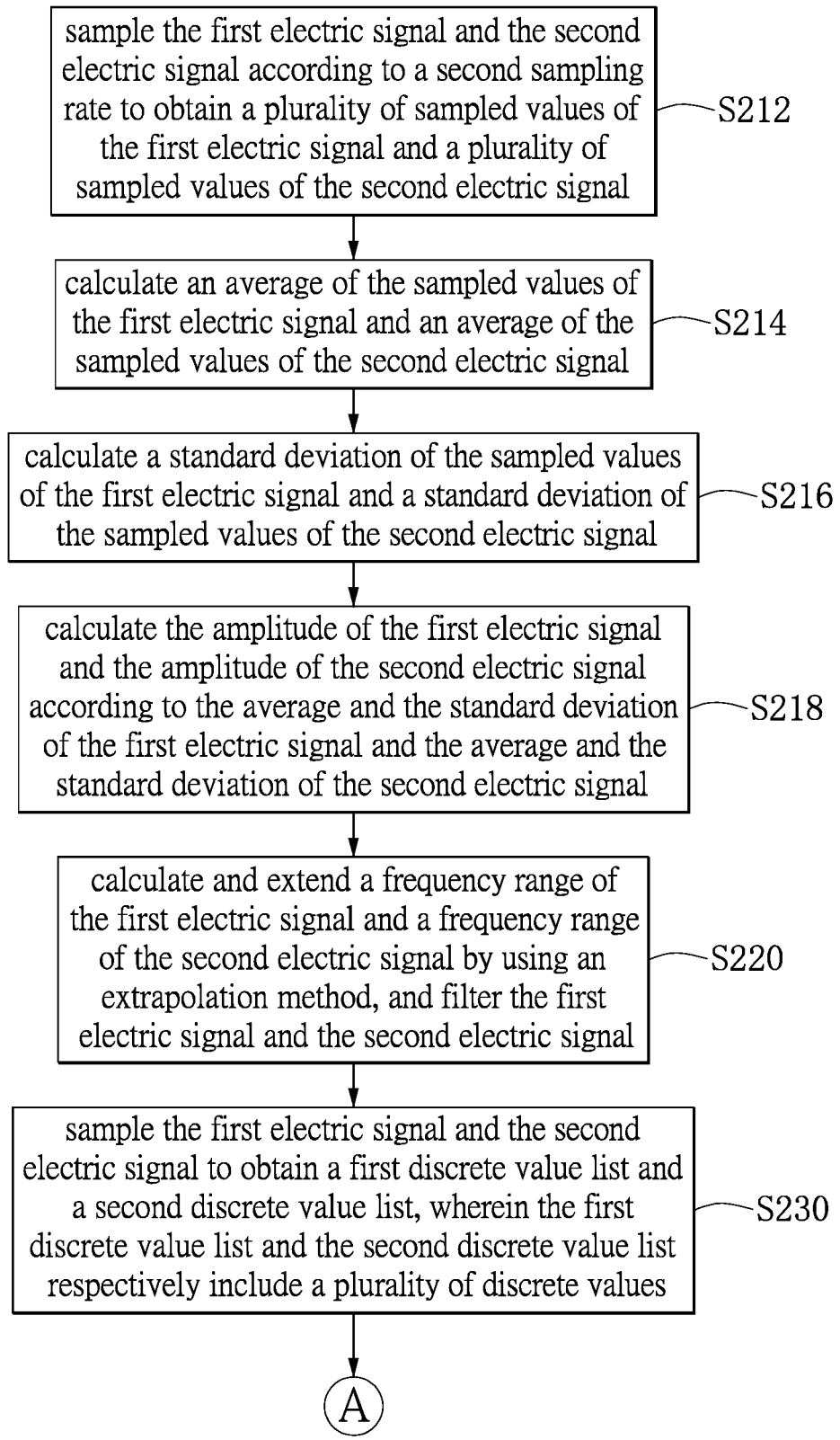
Figure 6B:
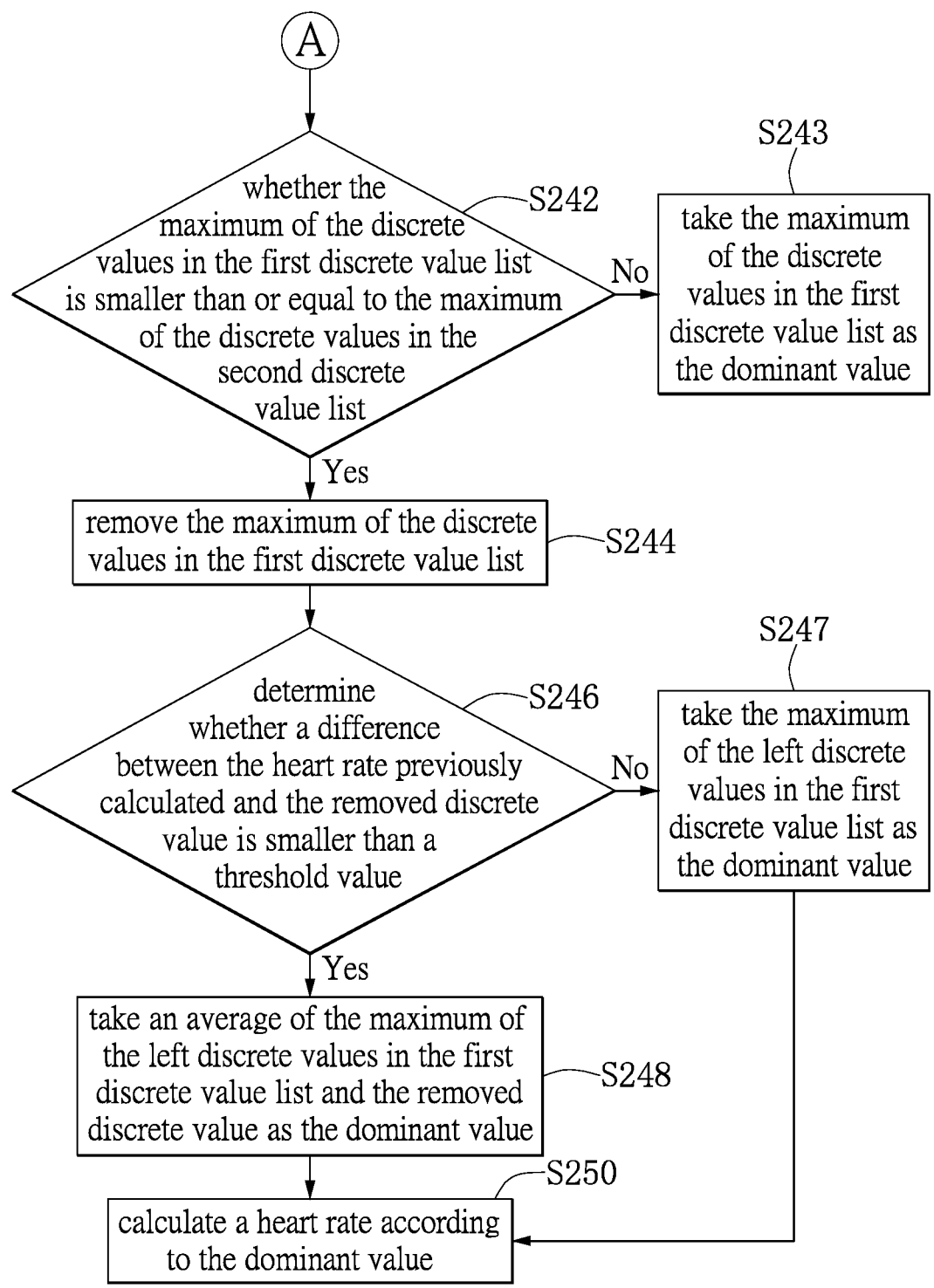

FIG. 5, FIG. 6A and FIG. 6B are flow charts showing steps of the heart rate calculation executed by the processor of the heart rate detection system in FIG. 4.

In this embodiment, the processor 16 calculates the heart rate of the user according to the first electric signal generated by the light sensor 14 and the second electric signal generated by the motion sensor 15, so that the processor 16 will first execute the step S210 which helps to do calculations for the first electric signal and the second electric signal. As shown in FIG. 5, the processor 16 executes the step S210 to normalize the first electric signal and the second electric signal such that the amplitude of the first electric signal and the amplitude of the second electric signal become equal. It should be noted that, before executing the step S210, the processor 16 converts the first electric signal and the second electric signal from time-domain signals to frequency-domain signals.

As shown in FIG. 6-1 and FIG. 6-2, the step S210 can be further divided into the steps S212~S218. In the step S212, the processor 16 samples the first electric signal and the second electric signal respectively. In this embodiment, the processor 16 samples the first electric signal and the second electric signal according to a second sampling rate. After sampling the first electric signal and the second electric signal, the processor 16 obtains a plurality of sampled values of the first electric signal and a plurality of sampled values of the second electric signal. After that, in the steps S214~S216, the processor 16 calculates an average of the sampled values of the first electric signal and an average of the sampled values of the second electric signal, and calculates a standard deviation of the sampled values of the first electric signal and a standard deviation of the sampled values of the second electric signal. Finally, in the step S218, the processor 16 calculates the amplitude of the first electric signal and the amplitude of the second electric signal according to the average and the standard deviation of the first electric signal, and the average and the standard deviation of the second electric signal. When the processor 16 completes the step S218, the first electric signal and the second electric signal will have been normalized.

Further, to have enough data for calculation, in the step S220, the processor 16 calculates and extends a frequency range of the first electric signal and a frequency range of the second electric signal by using an extrapolation method. In this embodiment, the processor 16 uses the Extrapolation by Reflection method to extend the frequency range of the first electric signal and the frequency range of the second electric signal. After that, the processor 16 filters the first electric signal and the second electric signal, which helps to do the following signal process.

In the step S230, the processor 16 samples the filtered first electric signal and the filtered second electric signal to obtain a first discrete value list and a second discrete value list. It should be noted that, the first discrete value list and the second discrete value list respectively include a plurality of discrete values. The discrete values in the first discrete value list are the signal data obtained after the processor 16 samples the filtered first electric signal. Likewise, the discrete values in the second discrete value list are the signal data obtained after the processor 16 samples the filtered second electric signal. In this embodiment, the processor 16 uses the DFT (Discrete Fourier Transform; DFT) method to sample the filtered first electric signal and the filtered second electric signal and obtain the first discrete value list and the second discrete value list.

As mentioned, the heart rate detection system provided by this embodiment takes the motion data of the human body (i.e. the second electric signal) captured by a motion sensor as a comparison data to find noises in the first electric signal, and then removes the noises. To accomplish this, in the step S240, the processor 16 calculates a dominant value according to the discrete values in the first discrete value list and the discrete values in the second discrete value list, and this dominant value is related to the heart rate of the user.

How the processor 16 calculates the heart rate of the user according to the discrete values in the first discrete value list and the discrete values in the second discrete value list is illustrated in the following descriptions. As shown in FIG. 6-1 and FIG. 6-2, the step S240 can be further divided into the steps S242~S248. In brief, the processor 16 executes the steps S242~S248 to compare the discrete values in the first discrete value list with the discrete values in the second discrete value list, and then accordingly removes the noises and determines the dominant value of the heart rate of the user.

In the step S242, the processor 16 determines whether the maximum one of the discrete values in the first discrete value list is smaller than or equal to the maximum one of the discrete values in the second discrete value list. When the maximum one of the discrete values in the first discrete value list is larger than the maximum one of the discrete values in the second discrete value list, the processor 16 executes the step S243 to determine the maximum one of the discrete values in the first discrete value list as the dominant value. On the other hand, when the maximum one of the discrete values in the first discrete value list is smaller than or equal to the maximum one of the discrete values in the second discrete value list, it indicates that the noises in the first electric signal are enough to interfere the signal actually related to the heart rate of the user. In this case, the processor 16 executes the step S244 to remove the maximum one of the discrete values in the first discrete value list.

However, to more precisely determine how the noises in the first electric signal can interfere the signal actually related to the heart rate of the user, the processor 16 further executes the step S246. In the step S246, the processor 16 determines whether a difference between the heart rate previously calculated and the discrete value removed in the step S244 is smaller than a threshold value. For example, the threshold value can be set as 12. In this example, when the difference between the heart rate previously calculated and the removed discrete value is larger than or equal to 12, it indicates that the discrete value removed in the step S244 is a noise. As a response, the processor 16 executes the step S247 to take the maximum one of the remaining discrete values in the first discrete value list as the dominant value. On the other hand, when the difference between the heart rate previously calculated and the removed discrete value is smaller than 12, it indicates that the discrete value removed in the step S244 is partially affected by the noises. As a response, the processor 16 executes the step S248 to take an average of the maximum one of the remaining discrete values in the first discrete value list and the removed discrete value as the dominant value.

The noises in the first electric signal will be removed by the processor 16 according to the second electric signal, and the dominant value related to the heart rate of the user is determined by the processor 16 after the processor 16 has executed the steps S242~S248. After that, the processor 16 executes the step S250 to calculate the heart rate of the user according to the dominant value. In this embodiment, the processor 16 converts the dominant value to the heart rate of the user by using a second heart rate conversion equation, and the second heart rate conversion equation can be represented as below.

$$BPM = f_{selected} * 60$$

In this equation, $f_{selected}$ is the dominant value, which is the frequency selected by using DFT method.

The heart rate detection system provided by this embodiment takes the motion data of the human body captured by a motion sensor as a comparison data to find noises in the first electric signal, and then removes the noises. Therefore, the heart rate of the user can be more precisely calculated according to the first electric signal in which noises caused by body motions have been removed.

[One Embodiment of the Wearable Device]

Figure 7:
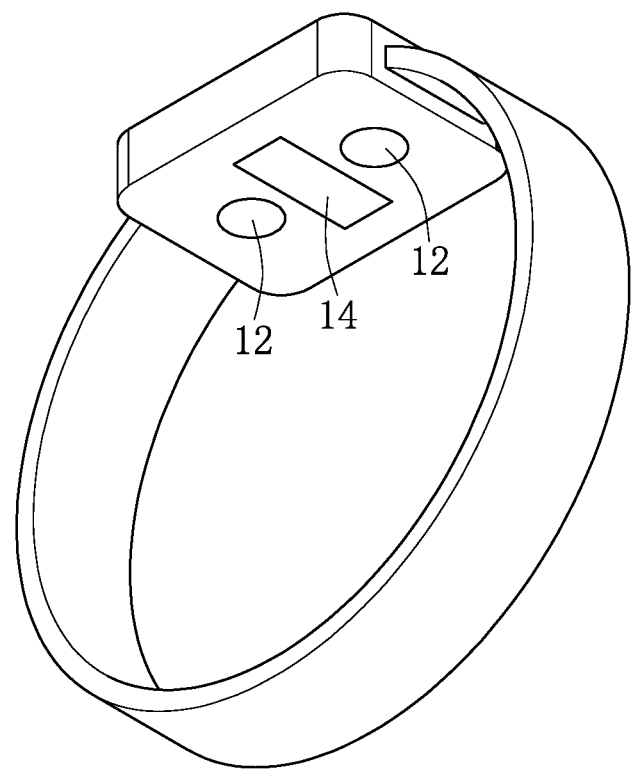
FIG. 7 shows a schematic diagram of a wearable device using a heart rate detection system according to one embodiment of the present disclosure.

The wearable device provided by this embodiment has any heart rate detection system provided by the above embodiments so that the wearable device is characterized by precise heart rate detection. FIG. 7 shows a schematic diagram of a wearable device using a heart rate detection system according to one embodiment of the present disclosure. For example, the wearable device can be a smart watch, a sports bracelet or the like. It should be noted that, where the wearable device should be worn is not restricted in the present disclosure, and other details relevant to the heart rate detection system configured in the wearable device have been described in the above embodiments so that repeated descriptions are omitted herein.

According to the above descriptions, by using the heart rate detection system or the wearable device in the present disclosure, the electric signal generated by the light sensor can be calibrated. Specifically speaking, the low-frequency noise signal or the high-frequency noise signal caused by the environmental factors can be effectively removed from the electric signal generated by the light sensor. Therefore, the heart rate of the user can be calculated precisely according to the calibrated electric signal.

Moreover, by using the heart rate detection system or the wearable device in the present disclosure, the motion data of the human body can be captured by a motion sensor as a comparison data to find noises in the electric signal, and then the noises can be removed from the electric signal. Therefore, the heart rate of the user can be calculated more precisely because the noises caused by body motions have been removed from the electric signal generated by the light sensor.

The descriptions illustrated supra set forth simply the preferred embodiments of the present disclosure; however, the characteristics of the present disclosure are by no means restricted thereto. All changes, alterations, or modifications conveniently considered by those skilled in the art are deemed to be encompassed within the scope of the present disclosure delineated by the following claims.

What is claimed is:
1. A heart rate detection system, comprising:
at least one light emitting unit, emitting a light to a user's body;
a light sensor, sensing a reflected light of the light and accordingly generating a first electric signal; and
a processor, coupled to the light sensor and the light emitting unit, configured to:
convert the first electric signal from a time-domain signal to a frequency-domain signal;
calculate a first noise signal according to a first equation, and subtract the first noise signal from the first electric signal of the frequency-domain signal;
calculate a second noise signal according to a second equation, and subtract the second noise signal from the first electric signal of the frequency-domain signal having the first noise signal removed;
convert the first electric signal of the frequency-domain signal having the first noise signal and the second noise signal removed to a second time-domain signal;
execute a peak detection with respect to the first electric signal of the second time-domain signal having the first noise signal and the second noise signal removed according to a first sampling rate, and calculate a plurality of peak values of the first electric signal of the second time-domain signal having the first noise signal and the second noise signal removed; and
calculate a plurality of time intervals among the peak values according to the first sampling rate and the peak values, and calculate a heart rate based on the time intervals;
wherein the first equation is:

$$Y[i] = \frac{\sum_{j=0}^{M-1} X[i+j]}{M};$$

wherein Y[i] is the first noise signal, X[i+j] is the first electric signal of the frequency-domain signal, and M is a sampling number;
wherein the second equation is:

$$S[i] = \frac{\sum_{j=0}^{M-1} Z[i+j]}{M};$$

wherein S[i] is the second noise signal, and Z[i+j] is the first electric signal of the frequency-domain signal having the first noise signal removed.

2. The heart rate detection system according to claim 1, wherein the processor is further configured to:
examine a voltage value of the first electric signal of the second time-domain signal having the first noise signal and the second noise signal removed corresponding to each time unit, and the time unit is a reciprocal of the first sampling rate; and
end the peak detection after examining the voltage value of the first electric signal of the second time-domain signal having the first noise signal and the second noise signal removed corresponding to the last time unit;
wherein if one of the voltage values is larger than all of the voltage values corresponding to the last three time units and the next three time units and also larger than an average of the voltage values corresponding to all time units, the processor determines that the voltage value is one of peak values of the first electric signal of the second time-domain signal having the first noise signal and the second noise signal removed.

3. The heart rate detection system according to claim 2, wherein the processor is further configured to:
dividing a difference between every two adjacent peak values by the first sampling rate to calculate the time intervals among the peak values; and
calculating the heart rate according to the time intervals and a first heart rate conversion equation, and the first heart rate conversion equation is:

$$BPM = \frac{2*60}{T\left[\frac{n}{2}\right] + T\left[\frac{n}{2}+1\right]}$$

wherein BPM is the heart rate, T is the difference between two adjacent peak values, and n is the number of the peak values.

4. A wearable device, comprising the heart rate detection system according to claim 1 for instantly detecting the heart rate of the user wearing the wearable device.

5. The wearable device according to claim 4, wherein the processor is further configured to:
examine a voltage value of the first electric signal of the time-domain signal having the first noise signal and the second noise signal removed corresponding to each time unit, and the time unit is a reciprocal of the first sampling rate; and
end the peak detection after examining the voltage value of the first electric signal of the time-domain signal having the first noise signal and the second noise signal removed corresponding to the last time unit;
wherein if one of the voltage values is larger than all of the voltage values corresponding to the last three time units and the next three time units and also larger than an average of the voltage values corresponding to all time units, the processor determines that the voltage value is one of peak values of the first electric signal of the time-domain signal having the first noise signal and the second noise signal removed.

6. The wearable device according to claim 5, wherein the processor is further configured to:
dividing a difference between every two adjacent peak values by the first sampling rate to calculate the time intervals among the peak values; and
calculating the heart rate according to the time intervals and a first heart rate conversion equation, and the first heart rate conversion equation is:

$$BPM = \frac{2*60}{T\left[\frac{n}{2}\right] + T\left[\frac{n}{2}+1\right]}$$

wherein BPM is the heart rate, T is the difference between two adjacent peak values, and n is the number of the peak values.

* * * * *